US009238599B2

(12) United States Patent
Winsett

(10) Patent No.: US 9,238,599 B2
(45) Date of Patent: Jan. 19, 2016

(54) ALKYLAROMATIC PROCESS

(75) Inventor: Beth A. Winsett, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 251 days.

(21) Appl. No.: 13/313,380

(22) Filed: Dec. 7, 2011

(65) Prior Publication Data

US 2013/0150607 A1 Jun. 13, 2013

(51) Int. Cl.
| | |
|---|---|
| C07C 2/66 | (2006.01) |
| C07C 17/275 | (2006.01) |
| C07C 201/12 | (2006.01) |
| C07C 41/30 | (2006.01) |
| C07C 319/20 | (2006.01) |
| C07C 68/06 | (2006.01) |
| C07C 209/68 | (2006.01) |
| C07C 67/343 | (2006.01) |
| C07C 37/11 | (2006.01) |
| C07C 45/68 | (2006.01) |
| C07C 15/02 | (2006.01) |
| C07C 15/24 | (2006.01) |
| C07C 319/12 | (2006.01) |
| C07C 15/28 | (2006.01) |
| C07C 15/38 | (2006.01) |
| C07C 25/02 | (2006.01) |
| C07C 37/14 | (2006.01) |
| C10M 105/06 | (2006.01) |
| C10M 177/00 | (2006.01) |
| C10M 109/02 | (2006.01) |

(52) U.S. Cl.
CPC . *C07C 2/66* (2013.01); *C07C 15/02* (2013.01); *C07C 15/24* (2013.01); *C07C 15/28* (2013.01); *C07C 15/38* (2013.01); *C07C 25/02* (2013.01); *C07C 37/14* (2013.01); *C10M 105/06* (2013.01); *C10M 109/02* (2013.01); *C10M 177/00* (2013.01); *C10M 2203/065* (2013.01); *C10M 2205/22* (2013.01); *C10M 2205/223* (2013.01); *C10N 2270/00* (2013.01)

(58) Field of Classification Search
USPC ........... 558/280, 260; 560/103; 564/305, 409; 568/433, 58, 628, 63, 67, 736, 766, 568/790, 939; 570/182, 190; 585/24, 26, 585/446, 455
See application file for complete search history.

(56) References Cited

U.S. PATENT DOCUMENTS

| | | | | |
|---|---|---|---|---|
| 3,130,007 | A * | 4/1964 | Breck | 423/711 |
| 3,251,897 | A * | 5/1966 | Wise | 585/455 |
| 4,211,665 | A | 7/1980 | Pellegrini, Jr. | |
| 4,238,343 | A | 12/1980 | Pellegrini, Jr. | |
| 4,283,583 | A * | 8/1981 | Velenyi et al. | 585/467 |
| 4,522,920 | A * | 6/1985 | Thorsson et al. | 435/161 |
| 4,604,491 | A | 8/1986 | Dressler et al. | |
| 4,663,492 | A * | 5/1987 | Chester et al. | 585/408 |
| 4,665,275 | A | 5/1987 | Yoshida et al. | |
| 4,694,114 | A * | 9/1987 | Chu et al. | 585/481 |
| 4,714,794 | A | 12/1987 | Yoshida et al. | |
| 4,737,297 | A | 4/1988 | Yoshida et al. | |
| 4,752,596 | A * | 6/1988 | Bergna et al. | 502/64 |
| 5,019,670 | A | 5/1991 | Lêet al. | |
| 5,034,563 | A | 7/1991 | Ashjian et al. | |
| 5,177,284 | A * | 1/1993 | Le et al. | 585/455 |
| 5,191,134 | A | 3/1993 | Le | |
| 5,254,274 | A | 10/1993 | Ho et al. | |
| 5,292,978 | A | 3/1994 | Solofo et al. | |
| 5,342,532 | A | 8/1994 | Takei et al. | |
| 5,602,086 | A * | 2/1997 | Le et al. | 508/591 |
| 6,010,617 | A | 1/2000 | Mackerer et al. | |
| 6,200,464 | B1 * | 3/2001 | van Houtert et al. | 208/119 |
| 2,132,156 | A1 | 9/2008 | Yoon et al. | |
| 2005/0277795 | A1 * | 12/2005 | Ghosh et al. | 585/467 |

FOREIGN PATENT DOCUMENTS

| | | |
|---|---|---|
| CA | 2076503 | 2/1993 |
| EP | 1 916 289 A1 | 4/2008 |
| FR | 2 662 438 | 11/1991 |
| WO | 91/15443 | 10/1991 |
| WO | 02/26671 | 4/2002 |
| WO | 2010/104581 | 9/2010 |

OTHER PUBLICATIONS

Yasuda et al. (Catalysis Today 50, (1999), 63-71).*
Zheng, J et al. (Fuel Processing Technology 89 (2008) 467-474).*
Smirniotis, P et al. (Ind. Eng. Chem. Res. 1994, 33, 800-813).*
J. Igarashi et al.,Autoxidation of Alkylnaphthalenes, 1. Self-Inhibition during the Autoxidation of 1- and 2-Methylnaphthalenes Puts a Limit on the Maximum Possible Kinetic Chain Length, J. Am. Chem. Soc, 1992, vol. 114, pp. 7719-7726.
J. Igarashi et al.,Autoxidation of Alkylnaphthalenes, 2. Inhibition of the Autoxidation of n-Hexadecane at 160° C., J. Am. Chem. Soc, 1992, vol. 114, pp. 7727-7736.
Hourani et al., Alkylated Naphthalenes as High-Performance Synthetic Lubricating Fluids, Tribology Transactions, 2007, vol. 50, pp. 82-87.

* cited by examiner

*Primary Examiner* — Sabiha N Qazi
(74) *Attorney, Agent, or Firm* — Leandro Arechederra, III; Luke A. Parsons

(57) ABSTRACT

This invention is directed to a new process for making an alkylaromatic compound. In an embodiment of this invention, the process is directed to selective synthesizing an alkylaromatic compound comprising a high amount of dialkylate product. In general, this process involves contacting at least one alkylatable aromatic compound with an alkylating agent and a catalyst under suitable reaction conditions such that the resulting reactor effluent prior to any stripping step may be characterized by a dialkylate product content of at least 44 wt % and a trialkylate and higher polyalkylate product content of no more than 20 wt %. The alkylaromatic compounds produced have excellent thermal and oxidative stabilities, good additive solvency, and improved seal compatibility while maintaining good VI and low temperature properties. They are useful as lubricant basestocks and lubricant additives.

13 Claims, No Drawings

ALKYLAROMATIC PROCESS

FIELD OF THE INVENTION

This disclosure relates to a new process for the production of alkylaromatic compounds useful as lubricant basestocks and lubricant additives.

BACKGROUND

Efforts to improve mineral oil lubricants by the use of oligomeric hydrocarbon fluids have been the subject of research and development for many years and have led to the market introduction of a number of poly alpha olefin (PAO) synthetic lubricants. Significant research on PAOs has been toward developing fluids that exhibit useful viscosities over an extended temperature range while also showing good lubricity, thermal and oxidative stability, and pour point. PAOs generally operate over a wider range of operating conditions than mineral oil lubricants, and may also exhibit lower friction and thus increase the mechanical efficiency of the equipment in which they are used.

PAOs can be produced by reacting an olefin feed in the presence of an acidic alkylation catalyst such as $AlCl_3$, $BF_3$, promoted $BF_3$, a metallocene, or other suitable oligomerization catalyst. PAOs are saturated hydrocarbon compositions and thus generally less polar than mineral oil compositions because the latter are unsaturated and may contain polar moieties. Thus, to improve the solvency and dispersancy of PAO compositions, a polar co-basestock such as an ester or alkylaromatic may be added to the composition. The polar co-basestock, however, could also introduce undesirable side effects. If an ester co-basestock is used, it may result in hydrolytic instability of the composition. If an alkylaromatic co-basestock is used, it may result in poor low temperature or reduced cleanliness properties of the composition.

Alkylaromatic compounds have been known for many years. They possess good thermal and oxidative stabilities, as disclosed in U.S. Pat. Nos. 4,211,665; 4,238,343; 4,604,491; and 4,714,794. These compounds, however, generally have poor rheological properties. Specifically, they have low viscosity indexes (VIs), consistent with their aromatic character. Thus, they are useful as heat transfer and functional fluids due to their good thermal and oxidative stabilities, but are otherwise generally disappointing as lubricants.

U.S. Pat. Nos. 5,254,274 and 5,019,670 disclose methods of improving the thermal and oxidative stabilities of PAOs by alkylating unsaturated oligomers with an aromatic compound. The products have improved stability and solvency due to the aromatics component as well as improved rheological characteristics. U.S. Pat. Nos. 4,737,297; 4,714,794; and 4,665,275 disclose various monoalkylate compounds with good oxidative stability and U.S. Pat. No. 5,342,532 discloses a mono- or dialkylate benzothiophene with good oxidative stability. U.S. Pat. No. 5,177,284 discloses making an alkylated naphthalene fluid with improved thermal and oxidative stability using low alkylation temperatures and low acidity zeolite catalysts. U.S. Pat. No. 5,602,086 discloses blends of alkylaromatics with PAOs to improve oxidation stability, solubility, elastomer compatibility, and hydrolytic stability.

Despite many improvements, current industry trends are demanding even better lubricant performance and in turn adding to the complexity of formulating lubricant compositions. In automotive applications, for example, the trend is toward extending oil drain intervals and improving fuel economy. In industrial applications, the trend is toward increasing oil drain intervals and extending equipment life. New lubricant compositions with improved properties are needed to meet these new performance requirements. Specifically, there is a need for alkylaromatics with an improved balance of thermal and oxidative stabilities, seal compatibility, solvency, and other properties.

Alkylaromatics, and specifically alkylated naphthalenes, are currently marketed in several viscosity grades. Alkylated naphthalenes currently on the market comprise of either: 1) a majority of monoalkylate with some dialkylate or 2) a distribution of mono-, di-, tri-, and higher poly-alkylates. Lower viscosity alkylated naphthalenes, with kinematic viscosities below about 6 cSt at 100° C., generally fall into category 1 and, thus, comprise primarily monoalkylates. Higher viscosity alkylated naphthalenes, with viscosities above about 6 cSt at 100° C., generally fall into category 2 and comprise a distribution of alkylates and a generally lower level of monoalkylates than lower viscosity alkylated naphthalenes.

The different compositions of the lower and higher viscosity alkylated naphthalenes result in a tradeoff of beneficial properties. Whereas lower viscosity grades generally have good oxidation stability, they may be incompatible with some seal materials due to the high level of monoalkylate. This is thought to be due to the porous nature of seal materials, wherein the pores are large enough for lower molecular weight molecules and, thus, lower viscosity grades to penetrate them. This penetration causes softening of the seals and seal swell, both undesirable in lubricant applications. Although higher viscosity grades are less likely to have seal compatibility issues due to their larger size molecules, their oxidative stability and solvency is not as good as lower viscosity grades due to the increased level of alkylation. This increased level of alkylation means the molecules in higher viscosity grades have more positions available for oxidative attack. Furthermore, solvency is generally believed to be a function of aromatic content, with more aromatic content providing improved solvency. Thus, as the level of alkylation increases in higher viscosity grades, the aromatic content decreases and solvency in turn decreases.

A process to selectively synthesize a dialkylate product has been unknown in the art for several reasons. Shape selective catalysts with no acidity on the surface, such as sodium zeolite USY catalysts, have been used to make monoalkylate-rich compounds. Attempting to increase the level of dialkylate by increasing the olefin to aromatic ratio in the feed results in deactivation of the catalyst, presumably due to coking. The effect of this presumed coking may be somewhat overcome by using more catalyst, but very high levels of catalyst are required. Other zeolites with acidity on the surface are somewhat more selective to mono- and dialkylate formation; however, tri- and higher poly-alkylates are still formed and dimerization of the olefin becomes more prevalent.

Alkylaromatic compounds have been produced using Friedel-Crafts alkylation reactions, which involve the alkylation of an aromatic ring with an alkyl halide using a strong Lewis acid catalyst. The use of non-zeolite catalysts, such as aluminum chloride, clays, triflic acid, or other Brønsted or Lewis acids results in a distribution of mono-, di-, tri-, and higher poly-alkylates. Additionally, dimerization of the olefin can occur with these catalysts as well. Adjusting the stoichiometry in these processes to favor mono- and dialkylates over tri- and higher poly-alkylates results in a large amount of unreacted naphthalene, which is difficult to process. In any process, a distillation step could be applied to separate out mono- or tri- and higher poly-alkylates to yield essentially pure dialkylate, however this would be uneconomical in current processes given the relatively low selective formation of dialkylate in the product stream. Additionally, as molecular weight of the product increases, distillation generally becomes more difficult. Thus, it becomes more difficult to separate the dialkylates from tri- and higher poly-alkylates in the reactor effluent as more of these heavier products is formed.

SUMMARY OF THE INVENTION

This invention is directed to a new process to produce alkylaromatic compounds. In an embodiment of this invention, this process is directed to the selective synthesis of an alkylaromatic compound comprising a high amount of dialkylate product. In general, this process involves contacting at least one alkylatable aromatic compound with an alkylating agent and a catalyst under suitable reaction conditions wherein the resulting alkylaromatic compounds may be characterized by a dialkylate product content of at least 44 wt % and a tri- and higher poly-alkylate product content of no more than 20 wt %. In an embodiment of this invention, the catalyst is a low sodium zeolite USY catalyst. The alkylaromatic compounds produced have excellent thermal and oxidative stabilities, good additive solvency, and improved seal compatibility while maintaining good VI and low temperature properties. They are useful as lubricant basestocks and lubricant additives.

DETAILED DESCRIPTION OF THE INVENTION

In general, this invention involves alkylating an aromatic hydrocarbon or substituted aromatic hydrocarbons in the presence of a catalyst to selectively produce a dialkylate product.
Alkylating Agent Suitable alkylating agents include any aliphatic or aromatic organic compound having one or more available alkylating aliphatic group capable of alkylating the aromatic compound. The alkylating aliphatic group itself should have at least 6 carbon atoms, and preferably at least 10. Olefins containing from 2 to about 30 carbon atoms such as ethylene, propylene, butene, pentene, hexene, octene, decene, dodecene, tetradecene, and the like may be used. Branched olefins, such as trimers, tetramers, pentamers, etc. of light olefins such as ethylene, propylene, butylenes, etc. may also be used. Mixtures of such olefins may also be used. Other alkylating agents which may be used, although less easily, include alcohols (including monoalcohols, dialcohols, trialcohols, etc.) such as hexanols, heptanols, octanols, decanols, undecanols, and dodecanols; and alkyl halides such as hexyl chlorides, octyl chlorides, dodecyl chlorides; and higher homologs. However, the alkylating agents are most preferably linear alpha olefins (LAOs) containing from 8 to 16 carbon atoms including mixtures thereof. In an embodiment of this invention, the alkylating agent is selected from the group including 1-dodecene, 1-tetradecene, and 1-hexadecene.
Aromatic Compound Substituted and unsubstituted aromatic compounds may be used in the alkylation reaction. Suitable substituted aromatic compounds may contain one or more short chain alkyl groups containing up to about 8 carbon atoms. Suitable aromatic compounds include substituted and unsubstituted benzene and polynuclear aromatic compounds, particularly naphthalene, anthracene, phenanthracene, toluene, o,m,p-xylene, hemimel-litene, pseudocumene, ethylbenzene, n-propylbenzene, cumene, n-butylbenzene, isobutylbenzene, sec-butylbenzene, tert-butylbenzene, p-cymene, biphenyl, diphenylmethane, triphenyl methane, 1,2-diphenylethane, and similarly alkyl substituted naphthalenes and anthracenes; also phenol, catechol, acylphenol such as acetylphenol, carbonate esters such as phenyl methyl or ethyl carbonate and diphenyl carbonate, alkylphenol such as anisole, choloro- and bromo-benzene, aniline, acyl aniline such as acetanil-ide, methyl- and ethyl-benzoate, thiophenol and acylated thiophenol, nitrobenzene, diphenylether, diphenylsulfide and similarly substituted naphthalenes and anthracenes, in particular naphthols such as mono- and di-hydroxy naphthalene. Naphthalene is preferred. Methylnaphthalenes, as disclosed in PCT/US 2005/035837, are also preferred.
Catalyst The alkylation process is carried out in the presence of a catalyst, and preferably a zeolite catalyst. The molecular size of the alkylation products requires a relatively large pore size in the zeolite for the products to leave the zeolite. Useful zeolites may be characterized by the presence of 12-membered oxygen rings in the molecular structure and a constraint index of not more than 2, and in most cases not more than 1. A method for determining constraint index, the significance of the index, and values of typical zeolites is described in U.S. Pat. Nos. 4,016,218 and 4,861,932, to which reference is made for such details. Examples of zeolites that may be useful include faujasite, the synthetic faujasites (zeolites X and Y, U.S. Pat. Nos. 2,882,244 and 3,130,007, respectively), zeolite L, ZSM-4 (U.S. Pat. No. 3,923,639), ZSM-18 (U.S. Pat. No. 3,950,496), ZSM-20 (U.S. Pat. No. 3,972,983), and offretite.

Some intermediate pore size zeolites with 10-membered oxygen rings may be useful if their structure is not too highly constrained. Thus, zeolites such as ZSM-12 (constraint index is 2; U.S. Pat. No. 3,948,758) may be useful. Zeolites having a constraint index up to about 3 may be useful, although the activity may be dependent on the choice of alkylating agent, especially its chain length, a factor which imposes diffusion limitations on the choice of zeolite.

A highly useful zeolite is zeolite Y, and especially zeolite Y in the ultrastable form, usually referred to as USY. Zeolite USY is produced by the stabilization of zeolite Y by a procedure of repeated ammonium exchange and controlled steaming. Processes for the production of zeolite USY are described in U.S. Pat. Nos. 3,402,966; 3,923,192; and 3,449,070. Preferred USY zeolites include H-USY, which are USY zeolites characterized by large, generally spherical internal cavities linked tetrahedrally through pore openings defined by 12-member rings of oxygen atoms.

All of the patents referenced herein describing catalysts are incorporated herein by reference for the details of such descriptions.

The zeolite may be composited with a matrix material or binder which is resistant to the temperatures and other conditions employed in the alkylation process. Such materials include active and inactive materials and synthetic or naturally occurring zeolites as well as inorganic materials such as clays, silica and/or metal oxides such as alumina, silica or silica-alumina. The latter may be either naturally occurring or in the form of gelatinous precipitates or gels including mixtures of silica and metal oxides. Use of an active material in conjunction with the zeolite may change the conversion and/or selectivity of the catalyst. Inactive materials suitably serve as diluents to control the amount of conversion so that alkylation products can be obtained economically and orderly without employing other means for controlling the rate of reaction. Binders which may be incorporated to improve the crush strength and other physical properties of the catalyst under commercial alkylation operating conditions include naturally occurring clays, e.g., bentonite and kaolin as well as the oxides referred to above.

In an embodiment of this invention, the zeolite catalyst has low sodium content. Specifically, the catalyst has preferably no more than 3 wt % of $Na_2O$, preferably no more than 2 wt %, preferably no more than 1 wt %, preferably no more than 0.5 wt %, preferably no more than 0.1 wt %, and more preferably no more than 0.06 wt %. In an embodiment of this invention, the catalyst has a $SiO_2/Al_2O_3$ mole ratio of at least 10, preferably at least 30, and more preferably at least 50. In an embodiment of this invention, the catalyst may also be characterized by the existence of unit cells with a minimum dimension of at least 7 Å, preferably at least 15 Å, and more preferably at least 20 Å.

The catalyst wt % in the overall feed may vary widely, ranging from about 0.1 to about 90 wt %. In an embodiment of this invention, the catalyst wt % in the overall feed is no more than 10 wt %, no more than 8 wt %, no more than 6 wt %, or no more than 4 wt %. In an embodiment of this invention, the catalyst wt % in the overall feed is between 0.5 and 10 wt %, 0.5 and 8 wt %, 0.5 and 6 wt %, or 0.5 and 4 wt %. The stability of the catalyst may be increased by steaming. U.S. Pat. Nos. 4,663,492; 4,594,146; 4,522,929; and 4,429,176 describe conditions for the steam stabilization of zeolite catalysts, to which reference is made for description of such conditions.

Alkylation Process

The alkylation may be carried out in any number of suitable reaction zones, such as batch-type, typically employing a closed, pressurized, stirred reactor with an inert gas blanketing system, or a semi-continuous or continuous operation utilizing a fixed, fluidized, or moving bed catalyst system, such as a flow reactor containing a fixed bed of the catalyst composition. A continuous stirred tank reactor (CSTR) is also suitable, for example, a process in such a reactor where reactants and catalyst are fed to the reactor continuously and products are continuously removed. The reactants can be in either the vapor or the liquid phase and can be free from intentional admixture or dilution, or they can be brought into contact with the catalyst with the aid of carrier gases or diluents such as, for example, hydrogen or nitrogen.

Reaction conditions for the invention may comprise temperatures between −30° C. and 500° C., typically between 30° C. and 250° C., and more typically between 150° C. and 250° C., pressures between 20 kPa and 25,000 kPa, and a feed weight hourly space velocity (WHSV) of from about 0.1 hour$^{-1}$ to 100 hour$^{-1}$, more typically from about 0.5 hour$^{-1}$ to 10 hour$^{-1}$. The WHSV is based upon the total weight of active catalyst (and binder, if present). When using naphthalene as the aromatic compound, the pressure should be maintained at about 350 kPa or greater to prevent the naphthalene from subliming into the overhead of the alkylation reactor. The molar ratio of alkylating agent to aromatic compound may range from 0.1:1 to 10:1, typically from 1:1 to 5:1. In a preferred embodiment of this invention, it is at least 2:1.

A stripping step may optionally be applied to the product stream to remove at least a portion of unreacted aromatic compound, unreacted alkylating agent, and/or mono-alkylate product, and the stripped portion may be recycled back into the alkylation process. In the invention and this disclosure, "stripping" and "distillation" are considered interchangeable terms and processes.

Alkylaromatic Compounds

The alkylaromatic compounds produced comprise at least one of the structures shown below:

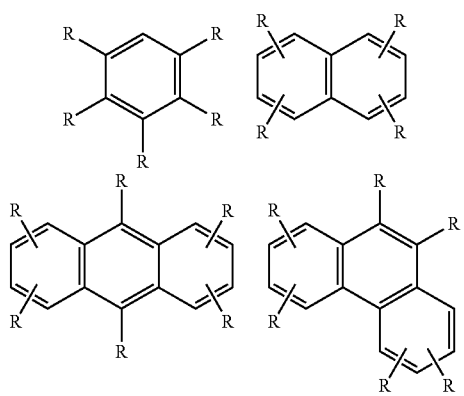

wherein at least one R group is an alkyl group remaining from the alkylation step. The remaining R groups are hydrogen or hydrocarbon groups such as cyclic or acyclic alkyl and alkenyl, aryl, $NH_2$, acylamido, halogen, acyl, alkoxycarbonyl, phenyl and YO or YS where Y is hydrogen, azyl, alkoxycarbonyl, phenyl, or cyclic or acyclic alkyl and alkenyl.

For purposes of clarity, when the alkylaromatic compounds comprise at least one of the structures shown below:

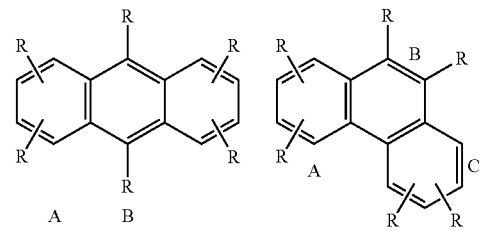

the third aromatic ring (existing at the position indicated by either "A" or "C" above, depending on how the aromatic rings are counted) is not considered an alkylation group for purposes of determining whether the product is a mono-, di-, tri-, or higher poly-alkylate. Thus, for example, if in either one of the structures above, two R groups are an alkyl group remaining from the alkylation step, the structure is considered a dialkylate and the third aromatic ring is considered part of the base structure, not a third substitution group.

In a preferred embodiment of this invention, the reactor effluent prior to any stripping step comprises at least 44 wt %, preferably at least 50 wt %, preferably at least 55 wt %, preferably at least 60 wt %, preferably at least 65 wt %, preferably at least 70 wt %, preferably at least 75 wt %, and more preferably at least 80 wt % of dialkylate product, wherein two of the R groups above are an alkyl group remaining from the alkylation step and the remaining R groups are hydrogen or hydrocarbon groups such as cyclic or acyclic alkyl and alkenyl, aryl, $NH_2$, acylamido, halogen, acyl, alkoxycarbonyl, and phenyl.

In a preferred embodiment of this invention, the reactor effluent prior to any stripping step also comprises no more than 30 wt %, no more than 25 wt %, no more than 20 wt %, no more than 15 wt %, no more than 10 wt %, no more than 5 wt %, no more than 2.5 wt %, and preferably 0 wt % of tri- and higher poly-alkylate products, wherein three or more of the R groups are an alkyl group remaining from the alkylation step and the remaining R groups are hydrogen or hydrocarbon groups such as cyclic or acyclic alkyl and alkenyl, aryl, $NH_2$, acylamido, halogen, acyl, alkoxycarbonyl, and phenyl.

In an embodiment of this invention, the reactor effluent prior to any stripping step also comprises no more than 20 wt %, no more than 15 wt %, no more than 10 wt %, no more than 5 wt %, no more than 2.5 wt %, and preferably 0 wt % of dimers of olefins used as alkylating agent in the reactor.

In an embodiment of this invention, the wt % ratio of monoalkylate to dialkylate product in the reactor effluent prior to any stripping step ranges from 50:50 to 10:90, preferably from 40:60 to 10:90, preferably from 30:70 to 10:90, and more preferably from 20:80 to 10:90.

In an embodiment of this invention, the reactor effluent comprises an alkylated benzene, alkylated naphthalene, alkylated methylnaphthalene, alkylated toluene, or alkylated phenol.

In an embodiment of this invention, the reactor effluent or the alkylaromatic compound produced have a kinematic viscosity at 100° C. between 2 cSt and 100 cSt.

The selective formation of compounds comprising a high amount of dialkylate product results in a new class of lubricant basestock with excellent thermal and oxidative stabilities, good additive solvency, and improved seal compatibility while maintaining VI and low temperature properties. These alkylaromatic compounds are useful as lubricant basestocks and lubricant additives, such as dispersants, detergents, viscosity index improvers, extreme pressure and antiwear additives, antioxidants, pour point depressants, emulsifiers, demulsifiers, corrosion inhibitors, rust inhibitors, antistaining additives, friction modifiers, and the like.

EXAMPLES

Kinematic viscosity was measured according to ASTM D 445. Viscosity index was measured according to ASTM D 2270. Color was measured on the ASTM scale according to ASTM D 1500. Pour point was measured according to ASTM D 97. The specific product composition of the reactor effluents was determined using Gas Chromatography, as generally described in "Modern Practice of Gas Chromatography", R. L. Grob and E. F. Barry, Wiley-Interscience, 3rd Edition (July 1995).

The ratio of monoalkylate to dialkylate to trialkylate and higher polyalkylate aromatic compounds may be referred to in this disclosure as the mono:di:tri ratio. The ratio of monoalkylate to dialkylate aromatic compounds may also be hereinafter referred to as the mono:di ratio. When these ratios are referenced, results are on a wt % basis unless otherwise noted. When the mono:di ratio is used in a particular example, the amount of trialkylate/higher polyalkylate aromatic compounds formed in that example was 0 wt % or less than what could be detected by measurement equipment. Conversion, when referenced herein, is defined as 100% minus the sum of the unreacted olefin wt % and the unreacted naphthalene wt %.

The MCM-family catalysts used in some of the examples are described in U.S. Pat. No. 5,236,575 (MCM-49) and U.S. Pat. No. 5,362,697 (MCM-56), and these descriptions are incorporated herein by reference.

Comparative Example 1

A feed of 1-hexadecene and naphthalene at a mole ratio of 1.6:1 was contacted in a semi-batch process with 1.5 wt % based on the weight of the overall feed of an USY catalyst with an $SiO_2/Al_2O_3$ mole ratio of 5.3, an $Na_2O$ wt % of 3.2, and a unit cell size of 24.53 (hereinafter "Comp 1"). The feed was added for one hour at 200° C. and then the feed was stopped and contents were allowed to react for one additional hour at 210° C. A representative portion of the reactor effluent was analyzed and found to contain a mono:di ratio of 93:7 and a dialkylate amount of 4.8 wt %, based on the wt % of the overall reactor effluent. The conversion was 71%.

Comparative Example 2

Comparative Example 2 was identical to Comparative Example 1 except that the catalyst was increased to 4.5 wt % based on the weight of the overall feed. A representative portion of the reactor effluent was analyzed and found to contain a 68:32 mono:di ratio and a dialkylate amount of 26.4 wt %, based on the wt % of the overall reactor effluent. The conversion was 83%.

Comparative Example 3

Comparative Example 3 was identical to Comparative Example 1 except that the catalyst was increased to 8 wt % based on the weight of the overall feed. A representative portion of the reactor effluent was analyzed and found to contain a mono:di ratio of 52:48 and a dialkylate amount of 43.9 wt %, based on the wt % of the overall reactor effluent. The conversion was 92%.

Comparative Example 4

Comparative Example 4 was identical to Comparative Example 1 except that the feed was 1-dodecene to naphthalene at a mole ratio of 2.4:1, and the catalyst was increased to 4 wt % of the overall feed. A representative portion of the reactor effluent was analyzed and found to contain a mono:di ratio of 60:40 and a dialkylate amount of 28.5 wt %, based on the wt % of the overall reactor effluent. The conversion was 71%.

Comparative Example 5

A feed of 1-hexadecene and naphthalene at a mole ratio of 2:1 was contacted in a semi-batch process with 4 wt % based on the weight of the overall feed of MCM-49/alumina catalyst (hereinafter "Comp 2"). The feed was added for one hour at 200° C. and then the feed was stopped and contents were allowed to react for one additional hour at 210° C. A representative portion of the reactor effluent was analyzed and found to contain a mono:di:tri ratio of 56:38:6 and a dialkylate amount of 28.9 wt %. The conversion was 80%. The reactor effluent also contained 4.3 wt % trialkylate and 3.6 wt % dimer, both based on the wt % of the overall reactor effluent, and the latter indicating that dimerization of the olefin had occurred.

Comparative Example 6

Comparative Example 6 was identical to Comparative Example 5 except that the catalyst was MCM-56/alumina (hereinafter "Comp 3") at 2 wt % of the overall feed. A representative portion of the reactor effluent was analyzed and found to contain a mono:di:tri ratio of 60:35:5 and a dialkylate amount of 29.8 wt %. The conversion was 88%. The reactor effluent also contained 4.6 wt % trialkylate and 3.6 wt % dimer, both based on the wt % of the overall reactor effluent, and the latter indicating dimerization of the olefin had occurred.

Comparative Example 7

A feed of 1-tetradecene and naphthalene at a mole ratio of 2.2:1 was contacted in a semi-batch process with 0.2 wt % based on the weight of the overall feed of a Friedel Crafts alkylation catalyst (hereinafter "Comp 4"). The feed was added slowly at a temperature of 160° C. and then the feed was stopped and contents were allowed to react for 1 hour. A representative portion of the reactor effluent was analyzed and found to contain a mono:di:tri ratio of 21:46:33 and a dialkylate amount of 44.1 wt %, based on the wt % of the overall reactor effluent. The conversion was 95%. This example shows that, while Friedel Crafts catalysts can form reactor effluents with a reasonably high amount of dialkylates, a significant amount of trialkylate is also formed.

Example 1

A feed of 1-hexadecene and naphthalene at a mole ratio of 1.6:1 was contacted in a semi-batch process with 2 wt % based on the weight of the overall feed of a low sodium USY catalyst with an $SiO_2/Al_2O_3$ mole ratio of 60, an $Na_2O$ wt % of 0.03, and a unit cell size of 24.24 (hereinafter "Cat 1"). The feed was added for one hour at 200° C. and then the feed was stopped and contents were allowed to react for one additional hour at 210° C. A representative portion of the reactor effluent was analyzed and found to contain a mono:di ratio of 51:49 and a dialkylate amount of 44.2 wt %, based on the wt % of the overall reactor effluent. The conversion was 89%. This result is surprising because the mono:di ratio and conversion are comparable to Comparative Example 3, where the feeds and process conditions were otherwise identical except that 8 wt % of catalyst was used. The catalyst surprisingly resulted in higher selectivity toward the dialkylate product.

Example 2

Example 2 was identical to Example 1 except that the 1-hexadecene to naphthalene mole ratio was 2:1 and the catalyst was increased to 4 wt % based on the weight of the overall feed. A representative portion of the reactor effluent was analyzed and found to contain a mono:di ratio of 37:63 and a dialkylate amount of 56.2 wt %, based on the wt % of the overall reactor effluent. The conversion was 90%. Increasing the catalyst amount thus resulted in an even more highly selective formation of the dialkylate product.

Example 3

Example 3 was identical to Example 1 except that the feed was 1-tetradecene to naphthalene at a mole ratio of 1.5:1 and the catalyst was 2 wt % based on the weight of the overall feed. A representative portion of the reactor effluent was analyzed and found to contain a mono:di ratio of 27:72 and a dialkylate amount of 64.2 wt %, based on the wt % of the overall reactor effluent. The conversion was 88%. Use of a lower molecular weight olefin feed thus surprisingly resulted in an even more highly selective formation of the dialkylate product.

Example 4

Example 4 was identical to Example 1 except that the feed was 1-tetradecene to naphthalene at a mole ratio of 2:1 and the catalyst was 4 wt % based on the weight of the overall feed. A representative portion of the reactor effluent was analyzed and found to contain a mono:di ratio of 17:83 and a dialkylate amount of 78.2 wt %, based on the wt % of the overall reactor effluent. The conversion was 94%.

Example 5

Example 5 was identical to Example 1 except that the feed was 1-dodecene to naphthalene at a mole ratio of 2:1 and the catalyst was 4 wt % based on the weight of the overall feed. A representative portion of the reactor effluent was analyzed and found to contain a mono:di ratio of 11:89 and a dialkylate amount of 87.1 wt %, based on the wt % of the overall reactor effluent. The conversion was 98%. Use of a lower molecular weight olefin feed thus again surprisingly resulted in an even more highly selective formation of the dialkylate product.

A stripping step could be applied to any of the reactor streams in these examples to separate the monoalkylate from the di- and trialkylate products. Applying such a step to the reactor streams in Examples 1-5 would be especially simple, and nearly pure dialkylate product could be economically obtained.

Another surprising result in Examples 1-5 was that, while very high ratios of dialkylates were obtained, little to no trialkylate was formed and dimerization of the olefin was not observed.

Example 6

A mixed feed of 1-hexadecene/1-tetradecene and naphthalene was contacted in a semi-batch process with 2 wt % of catalyst based on the weight of the overall feed. The catalyst was the same as the catalyst used in Examples 1-5. The 1-hexadecene/1-tetradecene was at a mole ratio of 1:1 and the 1-hexadecene/1-tetradecene to naphthalene was at a mole ratio of 2:1. The feed was added for one hour at 200° C. and then the feed was stopped and contents were allowed to react for one additional hour at 210° C. A representative portion of the reactor effluent was analyzed and found to contain a mono:di ratio of 38:62 and a dialkylate amount of 53.2 wt %, based on the wt % of the overall reactor effluent. The conversion was 86%.

Example 7

Example 7 was identical to Example 6 except that the catalyst was 4 wt % based on the weight of the overall feed. A representative portion of the reactor effluent was analyzed and found to contain a mono:di ratio of 18:82 and a dialkylate amount of 78.2 wt %, based on the wt % of the overall reactor effluent. The conversion was 95%.

Data from Comparative Examples 1-6 and Examples 1-7 is summarized in Table 1 below.

TABLE 1

Reaction Conditions from Examples 1-14

| Example | Catalyst | Olefin | Catalyst, wt % | Mono-alkylate, wt %[1] | Di-alkylate, wt %[1] | Tri-alkylate, wt %[1,2] | Dimer, wt %[1] | Mono:Di:Tri Ratio, wt % |
|---|---|---|---|---|---|---|---|---|
| Comparative 1 | Comp 1 | C16 | 1.5 | 66.4 | 4.8 | | | 93:7:0 |
| Comparative 2 | Comp 1 | C16 | 4.5 | 56.9 | 26.4 | | | 68:32:0 |
| Comparative 3 | Comp 1 | C16 | 8 | 48.1 | 43.9 | | | 52:48:0 |
| Comparative 4 | Comp 1 | C12 | 4 | 42.3 | 28.5 | | | 60:40:0 |
| Comparative 5 | Comp 2 | C16 | 4 | 43.1 | 28.9 | 4.3 | 3.6 | 56:38:6 |
| Comparative 6 | Comp 3 | C16 | 2 | 50.4 | 29.8 | 4.6 | 3.6 | 60:35:5 |
| Comparative 7 | Comp 4 | C14 | 0.2 | 21.0 | 46.0 | 33.0 | | 21:46:33 |
| 1 | Cat 1 | C16 | 2 | 45.3 | 44.2 | | | 51:49:0 |
| 2 | Cat 1 | C16 | 4 | 33.8 | 56.2 | | | 37:63:0 |
| 3 | Cat 1 | C14 | 2 | 24.6 | 64.2 | | | 27:72:0 |
| 4 | Cat 1 | C14 | 4 | 15.8 | 78.2 | | | 17:83:0 |
| 5 | Cat 1 | C12 | 4 | 10.9 | 87.1 | | | 11:89:0 |
| 6 | Cat 1 | C16/C14 | 2 | 32.8 | 53.2 | | | 38:62:0 |
| 7 | Cat 1 | C16/C14 | 4 | 17.0 | 78.2 | | | 18:82:0 |

[1]The sum of wt %'s of mono-, di-, and tri-alkylates and dimer is less than 100% due to unreacted materials in the effluent, which are not shown in this table.
[2]Where no result is shown, it does not imply that 0.0 wt % tri-alkylate was formed, but only that if any amount was formed, it was less than what could be detected by measurement equipment.

The reactor effluents from Examples 2, 4, 5, and 7 were sent through a distillation process to separate the respective dialkylate products, and these dialkylate products were further analyzed. Properties of these dialkylate products are summarized in Table 2 below.

TABLE 2

Analysis of the Stripped Dialkylate Products from Examples 2, 4, 5, and 7

| | Example 3 | Example 5 | Example 6 | Example 8 |
|---|---|---|---|---|
| KV at 100° C., cSt | 15.09 | 12.82 | 11.28 | 14.00 |
| KV at 40° C., cSt | 141.9 | 121.3 | 108.6 | 133.8 |
| VI | 108 | 98 | 88 | 101 |
| Color | 2.4 | 1.8 | 2.5 | 2.3 |
| Pour Point, ° C. | −27 | −45 | −42 | −36 |
| Monoalkylate, wt % | 0.05 | 0.07 | 0.10 | 0.05 |
| Dialkylate, wt % | 97.35 | 98.10 | 99.90 | 97.07 |
| Trialkylate, wt % | 2.61 | 1.83 | 0.00 | 2.88 |

What is claimed is:

1. A process to produce an alkylaromatic compound comprising contacting:
   a. at least one alkylatable aromatic compound;
   b. an alkylating agent; and
   c. a USY catalyst with a sodium content of no more than 1 wt % of $Na_2O$ and a $SiO_2/Al_2O_3$ mole ratio of at least 30; under alkylation conditions in a suitable reactor, wherein, prior to any stripping or distillation step, the reactor effluent stream comprises at least 44 wt % dialkylate product and no more than 20 wt % trialkylate and higher polyalkylate product.

2. The process according to claim 1 wherein the alkylatable aromatic compound is selected from the group including substituted and unsubstituted benzene and polynuclear aromatic compounds, toluene, o,m,p-xylene, hemimel-litene, pseudocumene, ethylbenzene, n-propylbenzene, cumene, n-butylbenzene, isobutylbenzene, sec-butylbenzene, tert-butylbenzene, p-cymene, biphenyl, diphenylmethane, triphenyl methane, 1,2-diphenylethane, phenol, catechol, acylphenols, carbonate esters, alkylphenols, choloro- and bromo-benzene, aniline, acyl anilines, methyl- and ethyl-benzoate, thiophenol and acylated thiophenol, nitrobenzene, diphenylether, diphenylsulfide, and naphthols.

3. The process according claim 1 wherein the alkylatable aromatic compound is selected from the group including naphthalene, methylnaphthalenes, and substituted naphthalenes.

4. The process according to claim 1 wherein the catalyst has a pore size of at least 7 Å.

5. The process according to claim 1 wherein the catalyst wt % in the feed is no more than 8 wt %.

6. The process according to claim 1 wherein the alkylation conditions comprise a temperature between −30° C. and 500° C. and a pressure between 20 and 25,000 kPa.

7. The process according to claim 1 wherein a stripping or distillation step is applied to the reactor effluent stream.

8. The process according to claim 1 wherein at least some portion of unreacted feed and/or monoalkylate product is recycled back to the reactor.

9. The process according to claim 1 wherein the amount of dialkylate product in the reactor effluent stream is at least 55 wt %.

10. The process according to claim 1 wherein the amount of trialkylate and higher polyalkylate product in the reactor effluent stream is no more than 10 wt %.

11. The process according to claim 1 wherein the reactor effluent stream comprises no more than 10 wt % of dimers of olefins used as alkylating agent in the reactor.

12. The process according to claim 1 wherein the wt % ratio of monoalkylate to dialkylate product in the reactor effluent stream prior to any stripping or distillation step ranges from 50:50 to 10:90.

13. The process according to claim 1 wherein the alkylaromatic compound has a kinematic viscosity at 100° C. between 2 cSt and 100 cSt.

* * * * *